United States Patent
Neff et al.

(10) Patent No.: US 9,944,568 B2
(45) Date of Patent: Apr. 17, 2018

(54) ENCAPSULATED FERTILIZER PARTICLE CONTAINING PESTICIDE

(71) Applicant: BASF SE, Ludwigshafen (DE)

(72) Inventors: Raymond A. Neff, Bloomfield Hills, MI (US); Alexander Gershanovich, Beverly Hills, MI (US); Johanne Wilson, Grosse Ile, MI (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/443,090

(22) PCT Filed: Nov. 15, 2013

(86) PCT No.: PCT/US2013/070270
§ 371 (c)(1),
(2) Date: May 15, 2015

(87) PCT Pub. No.: WO2014/078642
PCT Pub. Date: May 22, 2014

(65) Prior Publication Data
US 2015/0291481 A1    Oct. 15, 2015

Related U.S. Application Data

(60) Provisional application No. 61/727,282, filed on Nov. 16, 2012.

(51) Int. Cl.
| | | |
|---|---|---|
| C05G 3/00 | (2006.01) | |
| C05G 3/02 | (2006.01) | |
| C05C 9/00 | (2006.01) | |
| A01N 33/18 | (2006.01) | |
| A01N 25/26 | (2006.01) | |
| C08G 18/48 | (2006.01) | |
| C08G 18/66 | (2006.01) | |
| C09D 175/04 | (2006.01) | |
| C08G 18/32 | (2006.01) | |

(52) U.S. Cl.
CPC ........... *C05G 3/0029* (2013.01); *A01N 25/26* (2013.01); *A01N 33/18* (2013.01); *C05C 9/005* (2013.01); *C05G 3/02* (2013.01); *C08G 18/329* (2013.01); *C08G 18/4829* (2013.01); *C08G 18/6688* (2013.01); *C09D 175/04* (2013.01); *C08G 2310/00* (2013.01)

(58) Field of Classification Search
CPC ...... A01N 25/26; A01N 33/18; C09D 175/04; C05G 3/0029; C05G 3/02; C08G 18/4829; C08G 18/6688; C08G 18/329; C08G 2310/00; C05C 9/005
See application file for complete search history.

(56) References Cited

U.S. PATENT DOCUMENTS

| | | |
|---|---|---|
| 3,264,089 A | 8/1966 | Hansen |
| 4,588,803 A | 5/1986 | Christman |
| 4,711,659 A | 12/1987 | Moore |
| 4,804,403 A | 2/1989 | Moore |
| 5,219,465 A | 6/1993 | Goertz et al. |
| 5,300,135 A | 4/1994 | Hudson et al. |
| 5,411,856 A | 5/1995 | Riecke et al. |
| 5,423,897 A | 6/1995 | Hudson et al. |
| 5,429,654 A | 7/1995 | Swarup |
| 5,466,274 A | 11/1995 | Hudson et al. |
| 5,478,375 A | 12/1995 | Hudson |
| 5,538,531 A | 7/1996 | Hudson et al. |
| 5,599,374 A | 2/1997 | Detrick |
| 5,698,002 A | 12/1997 | Hudson |
| 5,750,130 A | 5/1998 | Ferrell et al. |
| 5,803,946 A | 9/1998 | Petcavich et al. |

(Continued)

FOREIGN PATENT DOCUMENTS

| | | |
|---|---|---|
| CN | 1636989 A | 7/2005 |
| CN | 101648837 A | 2/2010 |

(Continued)

OTHER PUBLICATIONS

EXTOXNET, Pesticide Information Profiles: Pendimethalin, 1996; obtained online on Aug. 3, 2016.*
International Search Report for Application No. PCT/US2013/041640 dated Oct. 8, 2013, 4 pages.
International Search Report for Application No. PCT/US2013/041571 dated Nov. 4, 2013, 4 pages.
International Search Report for Application No. PCT/US2013/070270 dated Feb. 18, 2014, 4 pages.
International Search Report for Application No. PCT/US2013/041630 dated Apr. 4, 2014, 3 pages.
English language abstract and machine-assisted English translation for JP 2006-298673 extracted from espacenet.com database on May 28, 2015, 19 pages.

(Continued)

*Primary Examiner* — Johann R Richter
*Assistant Examiner* — Genevieve S Alley
(74) *Attorney, Agent, or Firm* — DLA Piper LLP (US)

(57) ABSTRACT

An encapsulated particle comprises a core particle, a transferrable-pesticide disposed about the core particle, and a polyurethane layer disposed about the transferrable-pesticide. The core particle comprises a fertilizer, such as urea. The transferrable-pesticide can comprise a dinitroaniline, such as pendimethalin. The polyurethane layer is generally formed from a reaction mixture having a maximum temperature of no greater than about 30° C. The polyurethane layer inhibits the transferrable-pesticide from transferring to a surface different from the core particle when the encapsulated particle physically contacts the surface. A method of forming the encapsulated particle comprises the steps of encapsulating the core particle with the transferrable-pesticide to form an intermediate-particle, combining an isocyanate and a polyol to form the reaction mixture, and encapsulating the intermediate-particle with the reaction mixture to form the polyurethane layer of the encapsulated particle. The polyurethane layer comprises the reaction product of the isocyanate and polyol.

14 Claims, No Drawings

(56) References Cited

U.S. PATENT DOCUMENTS

| | | |
|---|---|---|
| 5,984,994 A | 11/1999 | Hudson |
| 5,993,505 A | 11/1999 | Tijsma et al. |
| 6,001,147 A | 12/1999 | Markusch et al. |
| 6,039,781 A | 3/2000 | Goertz et al. |
| 6,165,550 A | 12/2000 | Markusch et al. |
| 6,231,633 B1 | 5/2001 | Hirano et al. |
| 6,322,606 B1 | 11/2001 | Komoriya et al. |
| 6,358,296 B1 | 3/2002 | Markusch et al. |
| 6,359,031 B1 | 3/2002 | Lykke et al. |
| 6,364,925 B1 | 4/2002 | Markusch et al. |
| 6,380,133 B2 | 4/2002 | Becker et al. |
| 6,617,412 B2 | 9/2003 | Markusch et al. |
| 6,663,686 B1 | 12/2003 | Geiger et al. |
| 6,682,751 B1 * | 1/2004 | Hargrove ............... A01N 25/12 424/406 |
| 7,005,552 B2 | 2/2006 | Kaushiva |
| 7,018,440 B2 | 3/2006 | Tabei |
| 7,022,113 B2 | 4/2006 | Lockwood et al. |
| 7,267,707 B2 | 9/2007 | Rosenthal et al. |
| 7,416,785 B2 | 8/2008 | Mente |
| 7,452,399 B2 | 11/2008 | Whittington |
| 7,553,306 B1 | 6/2009 | Hunt et al. |
| 7,771,505 B2 | 8/2010 | Ogle et al. |
| 8,034,037 B2 | 10/2011 | Adams et al. |
| 8,303,680 B2 | 11/2012 | Mente |
| 2004/0115280 A1 | 6/2004 | Podszun et al. |
| 2004/0260230 A1 | 12/2004 | Randolph |
| 2005/0066697 A1 | 3/2005 | Cline et al. |
| 2005/0070858 A1 | 3/2005 | Lockwood et al. |
| 2005/0154359 A1 | 7/2005 | Charlez |
| 2005/0192548 A1 | 9/2005 | Dolliver et al. |
| 2005/0266245 A1 | 12/2005 | Mente |
| 2006/0032282 A1 | 2/2006 | Wynnyk et al. |
| 2006/0222735 A1 | 10/2006 | Rosenthal et al. |
| 2007/0100324 A1 | 5/2007 | Tempel et al. |
| 2007/0191538 A1 | 8/2007 | Apichatachutapan et al. |
| 2008/0125729 A1 | 5/2008 | Gradl |
| 2009/0012484 A1 | 1/2009 | Nielsen et al. |
| 2009/0221990 A1 | 9/2009 | Jaeb et al. |
| 2009/0240218 A1 | 9/2009 | Braga et al. |
| 2009/0264840 A1 | 10/2009 | Virginio |
| 2009/0292263 A1 | 11/2009 | Hudspeth et al. |
| 2009/0306630 A1 | 12/2009 | Locke et al. |
| 2009/0312728 A1 | 12/2009 | Randolph et al. |
| 2009/0326416 A1 | 12/2009 | McNulty et al. |
| 2009/0326488 A1 | 12/2009 | Budig et al. |
| 2010/0010477 A1 | 1/2010 | Augustine et al. |
| 2010/0011825 A1 | 1/2010 | Ogle et al. |
| 2010/0036333 A1 | 2/2010 | Schenk, III et al. |
| 2010/0055143 A1 * | 3/2010 | Terada ................ A01N 25/08 424/408 |
| 2010/0063463 A1 | 3/2010 | Wiesner |
| 2010/0069858 A1 | 3/2010 | Olson |
| 2010/0145289 A1 | 6/2010 | Lina et al. |
| 2010/0160853 A1 | 6/2010 | Smith et al. |
| 2010/0168688 A1 | 7/2010 | Santora et al. |
| 2010/0179493 A1 | 7/2010 | Heagle et al. |
| 2010/0185165 A1 | 7/2010 | Middleton et al. |
| 2010/0204663 A1 | 8/2010 | Wudyka |
| 2010/0210464 A1 | 8/2010 | Dunne et al. |
| 2010/0211030 A1 | 8/2010 | Turner et al. |
| 2010/0262091 A1 | 10/2010 | Larsson |
| 2010/0262096 A1 | 10/2010 | Hall |
| 2010/0268176 A1 | 10/2010 | Johnson et al. |
| 2010/0280422 A1 | 11/2010 | Hartwell |
| 2010/0286635 A1 | 11/2010 | Watson, Jr. |
| 2010/0286638 A1 | 11/2010 | Malhi |
| 2010/0298790 A1 | 11/2010 | Guidi et al. |
| 2010/0305523 A1 | 12/2010 | Vess |
| 2010/0326152 A1 | 12/2010 | Mente |
| 2011/0015590 A1 | 1/2011 | Svedman et al. |
| 2011/0022013 A1 | 1/2011 | Boynton et al. |
| 2011/0028921 A1 | 2/2011 | Hartwell et al. |
| 2011/0077605 A1 | 3/2011 | Karpowicz et al. |
| 2011/0105872 A1 | 5/2011 | Chickering, III et al. |
| 2011/0106027 A1 | 5/2011 | Vess et al. |
| 2011/0106030 A1 | 5/2011 | Scholz |
| 2011/0152799 A1 | 6/2011 | Kevin et al. |
| 2011/0196321 A1 | 8/2011 | Wudyka |
| 2011/0224631 A1 | 9/2011 | Simmons et al. |
| 2011/0270202 A1 | 11/2011 | Boehringer et al. |
| 2011/0276016 A1 | 11/2011 | Tsai |
| 2011/0288510 A1 | 11/2011 | Locke et al. |
| 2011/0295220 A1 | 12/2011 | Heaton et al. |
| 2013/0042659 A1 | 2/2013 | Beatty et al. |
| 2013/0305796 A1 | 11/2013 | Hudson et al. |
| 2013/0305797 A1 | 11/2013 | Neff et al. |
| 2013/0309499 A1 | 11/2013 | Neff et al. |

FOREIGN PATENT DOCUMENTS

| | | |
|---|---|---|
| CN | 102351608 A | 2/2012 |
| EP | 0 600 351 A1 | 6/1994 |
| EP | 0 867 422 A2 | 9/1998 |
| JP | S 58-205536 A | 11/1983 |
| JP | 2001-163691 A | 6/2001 |
| JP | 2003-104787 A | 4/2003 |
| JP | 2004-535276 A | 11/2004 |
| JP | 2006-265061 A | 10/2006 |
| JP | 2006-298673 A | 11/2006 |
| JP | 2008-133317 A | 6/2008 |
| JP | 2011-178650 A | 9/2011 |
| RU | 2 192 304 C2 | 11/2002 |
| RU | 2 234 839 C2 | 8/2004 |
| WO | WO 2006/105239 A2 | 10/2006 |
| WO | WO 2011/095859 A1 | 8/2011 |
| WO | WO 2012/151506 A1 | 11/2012 |
| WO | WO 2013/173705 A1 | 11/2013 |
| WO | WO 2013/173739 A2 | 11/2013 |
| WO | WO 2013/173748 A1 | 11/2013 |

OTHER PUBLICATIONS

BASF Corporation, "Pendulum Herbicide-Aquacap", 2009, pp. 1-19.

Scotts, "Scotts TurfBuilder with Halts Crabgrass Preventer, 30-0-4, Water Smart Formula", Material Safety Data Sheet, Jan. 17, 2008, pp. 1-4.

Database CA [Online] Chemical Abstracts Service, Columbus, Ohio, US; XP000406959, Database accession No. XP000406959, ISSN: 0009-2258, Dec. 2, 1991 (Dec. 2, 1991), 1 page.

English language abstract for CN 1636989 extracted from espacenet.com database on Dec. 17, 2015, 1 page.

Chen Wei, "Application Manual for Novel Process and Novel Technique of Up-To-Date Foam Plastics and Novel Formulations Thereof", Sep. 30, 2005, p. 722, with English language translation provided by CCPIT Patent on Dec. 22, 2015, 4 pages.

English language abstract and machine-assisted English translation for CN 101648837 extracted from espacenet.com database on Nov. 13, 2016, 18 pages.

English language abstract and machine-assisted English translation for CN 102351608 extracted from espacenet.com database on Jan. 12, 2017, 30 pages.

English language abstract and machine-assisted English translation for JPS 58-205536 extracted from espacenet.com database on Apr. 6, 2017, 7 pages.

English language abstract and machine-assisted English translation for JP 2006-265061 extracted from espacenet.com database on Apr. 6, 2017, 10 pages.

English language abstract and machine-assisted English translation for JP 2011-178650 extracted from espacenet.com database on Apr. 6, 2017, 31 pages.

English language abstract for RU 2 192 304 extracted from espacenet.com database on Apr. 24, 2017, 2 pages.

English language abstract for RU 2 234 839 extracted from espacenet.com database on Jul. 31, 2017, 2 pages.

English language abstract and machine-assisted English translation for JP 2001-163691 extracted from espacenet.com database on Aug. 28, 2017, 16 pages.

English language abstract for JP 2003-104787 extracted from espacenet.com database on Aug. 28, 2017, 1 page.

(56) References Cited

OTHER PUBLICATIONS

English language abstract and machine-assisted English translation for JP 2008-133317 extracted from espacenet.com database on Aug. 28, 2017, 14 pages.
Notice of Reasons for Refusal from corresponding Japanese Patent Application No. 2015-542812 along with its English translation; dated Jan. 9, 2018.

* cited by examiner

US 9,944,568 B2

ENCAPSULATED FERTILIZER PARTICLE CONTAINING PESTICIDE

CROSS REFERENCE TO RELATED APPLICATIONS

This application is the National Stage of International Patent Application No. PCT/US2013/070270, filed on Nov. 15, 2013, which claims priority to and all the advantages of U.S. Provisional Patent Application Ser. No. 61/727,282, filed on Nov. 16, 2012, the content of which is incorporated herein by reference in its entirety.

FIELD OF THE DISCLOSURE

The instant disclosure generally relates to an encapsulated particle, and more specifically to an encapsulated particle comprising a core particle, a transferrable-pesticide disposed about the core particle, and a polyurethane layer disposed about the transferrable-pesticide. The core particle comprises a fertilizer. The instant disclosure also relates to a method of forming the encapsulated particle.

BACKGROUND OF THE DISCLOSURE

Granular fertilizers are often coated with one or more herbicides before application/use of the granular fertilizers. Herbicides which are applied to granular fertilizers may be highly volatile, include natural or artificial pigment, and/or may not completely adhere to the granular fertilizer. One example of an herbicide often coated on granular fertilizers is pendimethalin. Pendimethalin is yellow in color and has a waxy to oily consistency, especially at temperatures approaching its melting point (~55° C.). Pendimethalin does not completely adhere to granular fertilizers to which it's applied, in part because of its consistency. Therefore, during handling, granular fertilizers coated with pendimethalin tend to transfer the pendimethalin to other surfaces, e.g. to clothes, skin, and/or application equipment, upon physical contact with the coated granular fertilizers. Residual pendimethalin, which collects on these surfaces, forms a yellow stain or film (comprising pendimethalin) that is very difficult to remove.

Additionally, the transfer of herbicides which are applied to granular fertilizers prior to application is problematic for a number of other reasons. Any transfer of herbicide off of the granular fertilizer is ultimately wasted, i.e., the herbicide does not reach its intended target. Additionally, herbicides which are transferred onto human skin or clothing pose a perceived (or an actual) health risk. Further, herbicides which are transferred onto surfaces of transportation and/or application equipment need to be removed, which leads to down time, cleaning expenses, etc.

Attempts to prevent the transfer of herbicides from granular fertilizers to other surfaces have included encapsulating the granular fertilizers having herbicides disposed thereon. However, conventional methods of encapsulation cause certain herbicides to sublime, melt, and/or vaporize. As such, conventional encapsulation methods are not suitable for certain herbicides, such as pendimethalin. Further, conventional encapsulants may inhibit controlled release of both the granular fertilizer and the herbicide upon application, due to excess encapsulant, inconsistent thickness of the encapsulant, and/or agglomeration of the encapsulated granular fertilizer, which result in waste and added expense. Accordingly, there remains an opportunity to provide improved encapsulated particles and methods of forming such encapsulated particles.

SUMMARY OF THE DISCLOSURE AND ADVANTAGES

Disclosed is an encapsulated particle. The encapsulated particle comprises a core particle, a transferrable-pesticide disposed about the core particle, and a polyurethane layer disposed about the transferrable-pesticide. The core particle comprises a fertilizer. The polyurethane layer is generally formed from a reaction mixture having a maximum temperature of no greater than about 30° C. The reaction mixture generally comprises an isocyanate and a polyol such that the polyurethane layer comprises the reaction product of the isocyanate and the polyol. The polyurethane layer inhibits the transferrable-pesticide from transferring to a surface different from the core particle when the encapsulated particle physically contacts the surface.

Also disclosed is a method of forming the encapsulated particle. The method comprises the step of encapsulating the core particle with the transferrable-pesticide to form an intermediate-particle. The method further comprises the steps of combining the isocyanate and the polyol to form the reaction mixture, and encapsulating the intermediate-particle with the reaction mixture to form the polyurethane layer of the encapsulated particle. The reaction mixture has a maximum temperature of no greater than about 30° C.

The isocyanate and the polyol react and cure to form the polyurethane layer, at a temperature which is generally below that which would sublime, melt, and/or vaporize the transferrable-pesticide (or a significant portion thereof). The isocyanate and polyol also impart excellent controlled release properties to the encapsulated particle. The polyurethane layer inhibits transfer of the transferrable-pesticide to other surfaces upon physical contact with the encapsulated particle. Further, the method promotes improved encapsulation of the core particle, consistent and minimal thickness of the polyurethane layer, increased yield, and minimized defects in the polyurethane layer. Increasing the yield and improving the quality of the encapsulated particle generally reduces the time and expense required to form the encapsulated particles. The encapsulated particles are useful for a variety of applications, such as for agricultural applications.

DETAILED DESCRIPTION OF THE DISCLOSURE

Disclosed is an encapsulated particle. The encapsulated particle comprises a core particle, a transferrable-pesticide disposed about the core particle, and a polyurethane layer disposed about the transferrable-pesticide. The transferrable-pesticide may be partially or completely disposed about the core particle. Said another way, the core particle may be partially or completely encapsulated by the transferrable-pesticide. Similarly, the polyurethane layer may be partially or completely disposed about the transferrable-pesticide and the core particle. Said another way, the transferrable-pesticide coated core particle (also referred to herein as an intermediate-particle) may be partially or completely encapsulated by the polyurethane layer. In certain embodiments, the intermediate-particle, i.e., the core particle and transferrable-pesticide, is completely encapsulated by the polyurethane layer. In these embodiments, the polyurethane layer protects the intermediate-particle and prevents undesired transfer of the transferrable-pesticide from the core particle to another surface.

The core particle comprises a fertilizer. Various types of fertilizers may be utilized as the core particle, and the core particle may comprise one, two, or more different type(s) of fertilizers. The instant disclosure is not limited to a particular type of fertilizer.

In certain embodiments, the fertilizer comprises calcium, magnesium, nitrogen, phosphate, potassium, sulfur, or combinations thereof. The fertilizer may also be selected from the group of nitrogenous fertilizers, phosphoric fertilizers, potash fertilizers, sulfuric fertilizers, and combinations thereof (e.g. mixed fertilizers). Suitable fertilizers also include anhydrous ammonia, urea, ammonium nitrate, urea ammonium nitrate, calcium ammonium nitrate, phosphoric acid, mono-ammonium phosphate, ammonium polyphosphate, ammonium phosphate sulfate, potash, ammonium nitrate, ammonium sulfate, sulfuric acid, or combinations thereof. In various embodiments, the fertilizer is a nitrogenous fertilizer, such as urea. In other embodiments, the fertilizer is ammonium sulfate. The core particle may further comprise one or more fertilizer adjuvants. While especially suitable for agricultural applications, the encapsulated particle is not limited to such use. For example, the encapsulated particle may be used in residential, commercial, and/or industrial applications. The encapsulated particles are generally provided for use as free-flowing particles. Said another way, the encapsulated particles are not typically in the form of a dispersion or solution, e.g. an aqueous solution or concentrate.

Although shape of the core particle is not critical, the core particle is typically spherical in shape. Accordingly, the core particle is typically either round or roughly spherical. The core particle may be of any size. In certain embodiments, the core particle has a particle size of from No. 170 mesh to about 5/16 inches, No. 35 to No. 3½ mesh, No. 18 to No. 5 mesh, or any size in between, as measured in accordance with standard sizing techniques using the United States Sieve Size Series. In other embodiments, the core particle has a particle size of from about 0.1 to about 10, about 0.1 to about 7, about 0.5 to about 5, about 1 to about 4, or about 1.5 to about 2.5, millimeters (mm), or any size in between. It is thought that core particles which are round or roughly spherical and have such particle sizes typically allow for a thinner and more uniform polyurethane layer (or layers) as compared to core particles having other particle shapes and/or sizes.

The transferrable-pesticide is generally capable of transferring to a surface different than the core particle upon physical contact with the surface. Said another way, the transferrable-pesticide may be of a phase/form which will transfer to the surface when the two come into contact. Typically, transfer of the transferrable-pesticide is sufficient to leave a residue on the surface which is clearly visible without technological aid. The residue is generally a portion of the original mass of the transferrable-pesticide, and can also be referred to as a stain or film comprising the transferrable-pesticide. The term "transfer" generally means that a portion of the transferrable-pesticide itself physically moves (i.e., a portion of mass) from the core particle to another surface.

The transferrable-pesticide is capable of transferring to surfaces different than the core particle at various temperatures, and such transference typically occurs at temperatures of about 30° C., alternatively at temperatures of about 25° C., or any temperature in between about 25 to about 30° C. For example, if the transferrable-pesticide is exposed to temperatures approaching its melting point, the transferrable-pesticide can undergo a phase change from solid to liquid (or thereabout) which promotes transfer of the transferrable-pesticide, such as by wicking, rubbing off, running off, etc., of the transferrable-pesticide to the surface.

The transferrable-pesticide may be in various forms, typically in a solid or liquid form, most typically in semi-solid or solid form. These phases/forms can include crystalline, waxy, and oily forms. In certain embodiments, the transferrable-pesticide is disposed within a carrier substance. In these embodiments, the carrier substance including the transferrable-pesticide is itself transferrable such that the carrier substance including the transferrable-pesticide will transfer to a surface different than the core particle upon physical contact with the surface.

The term "transferrable-pesticide" should not be interpreted to limit the transferrable-pesticide to a "mobile" pesticide which is either downwardly mobile (or "symplastically translocated") or upwardly mobile (or "apoplastically translocated") with respect to how these types of pesticides (e.g. herbicides) may move within a plant as understood in the art; however, certain pesticides may be categorized as such. For example, certain embodiments of the transferrable-pesticide may be categorized as contact pesticides, which are not mobile within a plant.

Further, the term "pesticide" refers to at least one active substance (or active ingredient) selected from the group of fungicides, insecticides, nematicides, herbicides, safeners, and/or growth regulators. As such, the transferrable-pesticide may also be referred to as a transferrable-fungicide, a transferrable-herbicide, etc. More typical pesticides for purposes of the instant disclosure are fungicides, insecticides, herbicides and growth regulators, and most typical are fungicides, herbicides, and growth regulators. Mixtures of two or more of the abovementioned pesticides may also be used. A skilled worker is familiar with such pesticides, which can be found, for example, in the Pesticide Manual, 15th Ed. (2009), The British Crop Protection Council, London. Certain chemistries may be defined or referred to herein as a particular type of pesticide, e.g. as a fungicide, but this does not mean that such pesticides are limited to such uses/applications. For example, a fungicide can also be used as an herbicide or vice versa. Overall, there is not complete consistency within the art as far as pesticide classification is concerned. The transferrable-pesticide may include additional components understood in the art, such as pesticide adjuvants, pigments, dyes, etc.

Referring back to the transferrable-pesticide, various types of insecticides may be utilized. Suitable insecticides include carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, and rotenone, or their derivatives.

In addition or alternate to insecticides, various types of fungicides may be utilized. Suitable fungicides include dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamide s, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, and triazoles.

In addition or alternate to insecticides and/or fungicides, various types of herbicides may be utilized. Suitable herbicides include acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, and ureas.

Further examples of suitable herbicides include: chloroacetamide herbicides, such as acetochlor, alachlor, butachlor, butenachlor, delachlor, diethatyl, dimethachlor, metolachlor, metolachlor-S, metazachlor, pretilachlor, propachlor, propisochlor, prynachlor, terbuchlor, thenylchlor, xylachlor, dimethenamid, dimethenamid-P; oxyacetamide herbicides, such as flufenacet and mefenacet; acetamide herbicides, such as diphenamid, napropamide and naproanilide; tetrazolinone herbicides, such as fentrazamide; arylurea herbicides, such as chlorbromuron, chlorotoluron, chloroxuron, dimefuron, diuron, ethidimuron, fenuron, fluometuron, isoproturon, isuron, linuron, methabenzthiazuron, metobromuron, metoxuron, monolinuron, neburon, siduron, tetrafluron and thebuthiuron; triazine herbicides, such as atrazine, chlorazine, cyanazine, cyprazine, eglinazine, ipazine, mesoprazine, procyazine, proglinazine, propazine, sebuthylazine, simazine, terbuthylazine and trietazine; triazin(di)one herbicides, such as ametridione, amibuzin, hexazinone, isomethiozin, metamitron and metribuzin; phenylcarbamate herbicides, such as desmedipham, phenisopham, phenmedipham and phenmediphamethyl; nitrile herbicides, such as bromobonil, bromoxynil, chloroxynil, dichlobenil, iodobonil and ioxynil; methylthiotriazine herbicides, such as ametryn, aziprotryne, cyanatryn, desmetryn, dimethametryn, methoprotryne, prometryn, simetryn and terbutryn; pyridazinone herbicides, such as norflurazon, brompyrazon, chloridazon, dimidazon, metflurazon, norflurazon, oxapyrazon and pydanon; pyridinecarboxamide herbicides, such as flufenican, diflufenican and picolinafen, beflubutamid, fluridone, flurochloridone and flurtamone; 4-HPPD inhibitors, such as isoxaflutole, mesotrione, tembotrione, topramezone and sulcotrione; pyridine herbicides, such as dithiopyr or thiazopyr; and herbicide safeners, such as benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloracetyl)-1,3-oxazolidine, 4-(dichloroacetyl)-1-oxa-4-azaspiro[4.5]decane and oxabetrinil; as well as their agriculturally acceptable salts and, provided they have a carboxyl group, their agriculturally acceptable derivatives.

In certain embodiments, the transferrable-pesticide comprises a dinitroaniline. Suitable dinitroanilines include benfluralin, butralin, chlornidine, dinitramine, dipropalin, ethalfluralin, fluchloralin, isopropalin, methalpropalin, nitralin, oryzalin, pendimethalin, prodiamine, profluralin, trifluralin, and mixtures thereof. In specific embodiments, the transferrable-pesticide is pendimethalin.

The transferrable-pesticide can have various vapor pressures. In certain embodiments, the transferrable-pesticide has a vapor pressure of greater than or equal to about 3, greater or equal to about 4, from about 3 to about 10, about 3 to about 8, about 3 to about 5, or about 3.5 to about 4.5, mPa at 25° C., or any vapor pressure in between. As understood in the art, the vapor pressure of a pesticide generally determines its volatility. Volatilization is the process whereby a pesticide changes from a liquid or solid to a gas. Volatile pesticides (those with higher vapor pressures) generally dissipate more rapidly than pesticides with lower vapor pressures. Volatilization generally increases with temperature and moisture. Most pesticides are relatively nonvolatile under normal field-use conditions. However, examples of volatile pesticides include members of the thiocarbamate family, such as EPTC (Eradicane®, Eptam®) and butylate (Sutan+); the dinitroanalines, trifluralin (Treflan®) and ethalfluralin (Sonalan®); and clomazone (Command®).

The transferrable-pesticide can have various melting points. In certain embodiments, the transferrable-pesticide has a melting point of from about 10 to about 100, about 10 to about 90, about 20 to about 80, about 30 to about 70, about 40 to about 65, about 50 to about 60, about 55 to about 60, or about 55, ° C., or any melting point in between.

The transferrable-pesticide can have various degrees of solubility in water. In certain embodiments, the transferrable-pesticide has the water-solubility of from about 0.01 to about 100, about 0.01 to about 50, about 0.01 to about 25, about 0.01 to about 20, about 0.01 to about 15, about 0.01 to about 10, about 0.01 to about 5, about 0.01 to about 1, about 0.1 to about 0.5, or about 0.3, mg/L at 20° C., or any water-solubility in between.

The polyurethane layer minimizes transfer of the transferrable-pesticide to surfaces different than the core particle upon physical contact with the surfaces. The polyurethane layer also ensures controlled release of both the core particle and the transferrable-pesticide upon application of the encapsulated particle. In various embodiments, the polyurethane layer is disposed on at least about 75, at least about 80, at least about 85, at least about 90, at least about 95, at least about 99, or at least 100, % of the core particle, or any % in between. Said another way, the intermediate-particle may be partially or completely encapsulated by the polyurethane layer.

The polyurethane layer may comprise a single layer or multiple sub-layers. In certain embodiments, the polyurethane layer comprises at least two sub-layers, at least three sub-layers, at least four sub-layers, at least five sub-layers, or at least six sub-layers. The sub-layers may be the same as or different from one another. Said another way, it is contemplated that the core particle can be encapsulated with at least one polyurethane sub-layer and one or more additional sub-layers including a material other than polyurethane. Alternatively, polyurethanes of differing type can be used to form the sub-layers.

Typically, the polyurethane layer (or collective sub-layers) has an average thickness of from about 5 to about 50, about 10 to about 40, or about 15 to about 35, microns, or any average thickness in between. The polyurethane layer can be utilized in various thicknesses depending on one or more desired properties, such as the dissolution rate of the encapsulated particle.

The polyurethane layer is generally formed from polyurethane as its name implies. As such, the polyurethane layer typically comprises the reaction product of an isocyanate and a polyol. The polyurethane layer may also be formed in the presence of other components.

The reaction mixture of the isocyanate and the polyol utilized to form the polyurethane layer has a maximum temperature of no greater than about 30° C., and more typically an initial (lowermost) temperature and a maximum (uppermost) temperature less than or equal to about 30° C. and alternatively less than or equal to about 25° C. In certain embodiments, the reaction mixture is at or about ambient or room temperature. Such temperatures prevent or minimize transfer of the transferrable-pesticide during encapsulation of the transferrable-pesticide. If temperatures are too high, certain transferrable-pesticides can undergo a phase change, such that they melt, vaporize, sublime, etc.

Typically, the reaction mixture is free of catalysts. Stated differently, the reaction mixture does not require catalysts to maintain an initial temperature and a maximum temperature. Quite simply, omitting catalysts helps keep the reaction mixture close to ambient temperature during reaction. However, catalyst(s), including polyols which may function in a manner similar to catalysts, may be present.

Individual components of the reaction mixture may be at higher temperatures than those described above, but the reaction mixture as a whole is generally at a lower temperature, e.g. no greater than about 30° C., during formation of the polyurethane. Aside from controlling the temperature of the starting components, e.g. individual reactants, and/or via the inclusion or exclusion of catalysts, temperature of the reaction mixture can also be controlled by physical means, such as via heat exchange. For example, a jacketed reactor/vessel may be utilized to remove exothermic heat as the reaction occurs. Other means understood in the art may also be used. The amounts of components and/or total reaction mass can also dictate the amount of heat generated or maintained during reaction. The core particle can also be used to control overall temperature of the reaction mixture. For example, the core particle can act as a heat sink when introduced at a temperature lower than that produced by the exothermic reaction between the isocyanate and the polyol. Quite simply, temperature of the reaction mixture can be controlled via various chemical and/or physical means.

Typically, the polyurethane layer has a glass transition temperature (Tg) of at least about 60, of from about 60 to about 100, about 70 to about 100, about 80 to about 100, or about 85 to about 95, ° C., or any Tg in between. It is thought that such Tg values reduce tack and therefore agglomeration of the encapsulated particles.

The isocyanate may comprise one or more isocyanates. Typically, the isocyanate is an aromatic isocyanate. In certain embodiments, the isocyanate includes monomeric and polymeric methylene diphenyl diisocyanate, monomeric and polymeric toluene diisocyanate, and mixtures thereof. Examples of suitable isocyanates are commercially available from BASF Corporation of Florham Park, N.J., under the trade name of LUPRANATE®.

In specific embodiments, the isocyanate is LUPRANATE® M20. Polymeric methylene diphenyl diisocyanates, such as LUPRANATE® M20, offer high crosslink density and moderate viscosity. Alternatively, monomeric methylene diphenyl diisocyanates such as LUPRANATE® M, offer low viscosity and high NCO content with low nominal functionality. Similarly, toluene diisocyanates, such as LUPRANATE® MP102, also offer low viscosity and high NCO content with low nominal functionality. Those skilled in the art will choose a suitable isocyanate based on the desired properties of the polyurethane layer formed therefrom.

Typically, the isocyanate has a viscosity of from about 1 to about 3,000, about 20 to about 1,000, or about 50 to about 300, centipoise (cP) at 25° C., or any viscosity in between. Isocyanates having low to moderate viscosities facilitate spraying of the isocyanate onto the core particle. The isocyanate typically has a nominal functionality of from about 1 to about 5, about 1.5 to about 4, about 2.0 to about 2.7, or any nominal functionality in between, which allows for effective reaction of the isocyanate with the polyol and improves cost efficiency. Typically, the isocyanate has an NCO content of from about 20 to about 50, about 25 to about 40, or about 30 to about 33, % by weight, or any NCO content in between. The NCO content provides a high molecular crosslink density that aids in the formation of the polyurethane layer. The NCO content also provides more chemical bonds per unit of mass to improve cost efficiency. The viscosity, the nominal functionality, and the NCO content of the isocyanate may vary outside of the ranges above, but are typically both whole and fractional values within those ranges. In certain embodiments, the isocyanate is utilized in an amount from about 40 to about 60, about 45 to about 55, or about 48 to about 52, % by weight, or any % in between, each based on the total weight of the isocyanate and polyol.

The polyol may comprise one or more polyols. The polyol typically includes polyols having at least two hydroxyl (OH) functional groups. In addition to OH functional groups, the polyol can include polyols having one or more amine functional groups.

As a whole, the polyol has various physical and chemical properties different from, yet dependent upon, the properties of the individual polyols included in the polyol. The polyol typically has a number average molecular weight (Mn) of from about 200 to about 850, about 300 to about 700, about 300 to about 600, or about 300 to about 500, g/mol. Typically, the polyol has a viscosity of from 100 to 1,000 cP at 25° C. The polyol typically has a nominal functionality of from about 2 to about 5, about 2 to about 4, or about 2.5 to about 3.5. Typically, the polyol has a OH number of from about 200 to about 600 and alternatively from about 300 to about 500, mg KOH/g. The Mn, viscosity, nominal functionality, and OH number of the polyol may be any value outside of the ranges above, but are typically both whole and fractional values within those ranges.

In specific embodiments, the polyol comprises a polyether polyol. The polyether polyol is typically formed from an initiator and a plurality of alkylene oxide units. In various embodiments, the plurality of alkylene oxide units comprises at least about 50% by weight propylene oxide (PO) units based on the total weight of the plurality of alkylene oxide units. Alternatively, the plurality of alkylene oxide units comprise at least about 50, at least about 60, at least about 70, at least about 80, at least about 90, at least about 95, or at least about 99, % by weight PO units, based on the total weight of the plurality of alkylene oxide units. Alternatively still, the plurality of alkylene oxide units may comprise 100% by weight PO units based on the total weight of the plurality of alkylene oxide units. Other alkylene oxide units include ethylene oxide (EO), butylene oxide (BO) units, etc.

In certain embodiments, the polyether polyol is an intermediate molecular weight, secondary hydroxyl terminated polyol. In this embodiment, the polyether polyol is typically initiated with at least one non-amine based, tri-functional initiator. Suitable initiators for initiating the polyether polyol of this embodiment include glycerine, trimethylolpropane, propylene glycol, dipropylene glycol, isopropylene glycol, sorbitol, sucrose, and the like. The polyether polyol typically has a Mn of from about 100 to about 1,000, and alternatively from about 200 to about 600, g/mol. Typically, the polyether polyol has a viscosity of from about 100 to about 1,000, about 150 to about 600, or about 300 to about 400, cP at 25° C. The polyether polyol typically has a nominal functionality of from about 2 to about 5, about 2 to about 4 or about 2.8 to about 3.2. Typically, the polyether polyol has a OH number of from about 200 to about 600, about 300 to about 500, or about 350 to about 450, mg KOH/g. The Mn, viscosity, nominal functionality, and OH number of the polyether polyol may be any value outside of the ranges above, but are typically both whole and fractional values within those ranges. A suitable polyether polyol for these embodiments is commercially available from BASF Corporation under the trade name of PLURACOL® GP430R. Other grades of PLURACOL® may also be utilized, in addition or alternate to, PLURACOL® GP430R.

In yet other embodiments, the polyol comprises a "catalytic" polyol. The catalytic polyol can be used instead of a catalyst to facilitate chemical reaction between the isocyanate and polyol. Said differently, a polyol that includes the catalytic polyol will typically chemically react with the isocyanate at lower temperatures in the presence of less catalyst (or no catalyst at all) relative to a polyol that does not include the catalytic polyol.

In certain embodiments, the catalytic polyol is derived from an aromatic amine-based initiator. The catalytic polyol may be formed with more than one initiator. In specific embodiments, the catalytic polyol is co-initiated with dipropylene glycol (DPG). Without being bound or limited by any particular theory, it is thought that amine content of the catalytic polyol facilitates reaction of the isocyanate and polyol.

The catalytic polyol may also include alkylene oxide substituents. Examples of suitable alkylene oxides substituents include EO, PO, BO, amylene oxide, mixtures thereof, alkylene oxide-tetrahydrofuran mixtures, epihalohydrins, and aralkylene styrene.

The catalytic polyol may be derived from an aromatic amine-based initiator. In various embodiments, the aromatic amine-based initiator is of the formula:

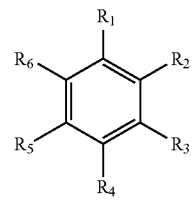

wherein $R_1$ includes one of an alkyl group, an amine group, and a hydrogen atom, and each of $R_2$ through $R_6$ independently include one of an amine group and a hydrogen atom, so long as at least one of $R_1$ through $R_6$ is an amine group. Therefore, $R_1$ can be any one of an alkyl group, an amine group, or a hydrogen atom, or any compound including combinations thereof. Each of $R_2$ through $R_6$ do not have to be identical and each can include an amine group or a hydrogen atom. It is also to be understood that the terminology "an amine group" refers to R—N—H and $NH_2$ throughout. The amine group can be primary or secondary.

The aromatic amine-based initiator may include a toluene diamine. Suitable examples of toluene diamine include the following formulas and mixtures thereof:

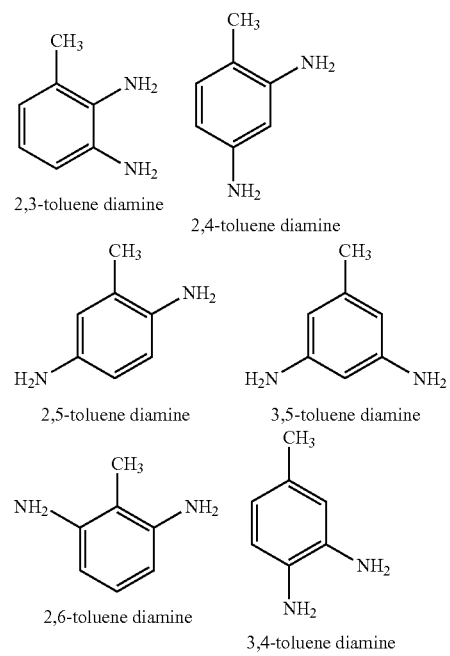

Without being bound or limited by any particular theory, it is thought that miscibility between the isocyanate and polyol minimizes formation of surface defects in the polyurethane layer of the encapsulated particle. For example, when a non-aromatic polyol is combined with an isocyanate such as an aromatic isocyanate, miscibility may be compromised. The non-aromatic polyol may react with the aromatic isocyanate in a partial manner only at an interface resulting in surface defects (e.g. pits and depressions) in polyurethane layers formed therefrom. The aromatic amine-based initiator tends to yield a catalytic polyol that is miscible with the isocyanate, e.g. completely miscible with the isocyanate.

It is thought that the miscibility of the isocyanate and catalytic polyol formed from an aromatic amine-based initiator tends to result from two primary effects. First, it is thought that the miscibility is affected by London Forces that create momentarily induced dipoles between similar aromatic moieties of the catalytic polyol and the isocyanate. The momentarily induced dipoles allow the catalytic polyol and the isocyanate to mix effectively. Secondly, it is thought that the miscibility is affected by the planar geometry of the aromatic moieties of the catalytic polyol and the isocyanate that allow for complementary stacking of the catalytic polyol and the isocyanate. As such, the isocyanate and catalytic polyol mix effectively.

Typically, the catalytic polyol formed from an aromatic amine-based initiator has a viscosity of from about 500 to about 10,000, about 2,000 to about 8,000, about 4,000 to about 6,000, or about 5,000 to about 6,000, cP at 25° C. Typically, the catalytic polyol has a nominal functionality of from about 2 to about 5, about 3 to about 5, or about 3.8 to about 4.2. The catalytic polyol typically has a OH number of from about 100 to about 700, about 300 to about 550, or about 400 to about 500, mg KOH/g. Typically, the catalytic polyol has a Mn of from about 240 to about 2,250, about 330 to about 1,120, or about 370 to about 900, g/mol. The viscosity, nominal functionality, OH number, and Mn of the catalytic polyol may vary outside of the ranges above, but are typically both whole and fractional values within those ranges. A suitable catalytic polyol is commercially available from BASF Corporation under the trade name of PLURACOL® 735.

In certain embodiments, the polyol includes both the catalytic polyol and the polyether polyol. In these embodiments, the polyether polyol is typically present in the polyol in an amount greater than the amount of the catalytic polyol. A weight ratio of the polyether polyol to the catalytic polyol in the polyol is typically of from about 1:2 to about 10:1, about 2:1 to about 10:1, about 2:1 to about 8:1, about 2.5:1 to about 6:1, about 5:1 to about 6:1, about 2:1 to about 4:1, about 2.5:1 to about 3.5:1, or about 1:2 to about 2:1. The weight ratio of the polyether polyol to the catalytic polyol may vary outside of the ranges above, but is typically both whole and fractional values within those ranges. In certain embodiments, the polyol is utilized in an amount from about 40 to about 60, about 45 to about 55, or about 48 to about 52, % by weight, or any amount in between, each based on the total weight of the isocyanate and polyol.

The properties of the polyol impact the properties of the polyurethane layer. The viscosity of the polyol impacts spraying of the polyol onto the core particle. The nominal functionality of the polyol impacts reaction of the polyol and isocyanate. The OH number of the polyol impacts cross-linking density of the polyurethane layer. Without being bound or limited by any particular theory, it is thought that the lower Mn of the polyol described above results in a polyol that is well suited for reacting with the isocyanate at a temperature of less than or equal to about 30° C. and alternatively less than or equal to about 25° C., to form a tack-free polyurethane having a Tg as described above. Polyols having a higher Mn can form tacky polyurethanes, leading to agglomeration while being formed. Polyols with higher nominal functionalities can form polyurethanes that are typically too "brittle". Further, the physical and chemical properties of the polyol contribute to optimal processing conditions, reaction speed, and non-agglomeration.

In certain embodiments, the polyol and/or isocyanate include(s) an oil. In various embodiments, the oil is soluble in the polyol including either the catalytic polyol derived from an aromatic amine-based initiator and/or the polyether polyol different from the catalytic polyol. In these embodiments, the oil may further minimize agglomeration of the encapsulated particle during coating and curing. The oil does not substantially chemically react with the isocyanate, polyol, or other optional liquids present during cure of the polyurethane. In other words, the oil is substantially free from substituent groups which are known to react with the polyol and/or isocyanate, such as OH groups and amine groups. In certain embodiments, less than about 10, less than about 5, less than about 1, less than about 0.5, or less than about 0.1, wt. % of a total amount of the oil present, reacts with the polyol, isocyanate, and/or the other optional liquids present during cure. Alternatively, in specific embodiments, none of the oil reacts with the polyol, the isocyanate, and/or the other optional liquids present during curing.

The oil can be added to the isocyanate, polyol, or may be added to a mixture of the isocyanate and polyol. Said another way, the reaction mixture can include the oil. Although not particularly limited, the oil may comprise soybean oil, canola oil, peanut oil, sunflower seed oil, cottonseed oil, methyl esters derived from vegetable oils, and combinations thereof. In specific embodiments, the oil comprises methyl esters derived from vegetable oils.

If utilized, the oil is typically present in an amount of from about 1 to about 30, about 5 to about 25, or about 10 to about 20, % by weight, each based on the total weight of the isocyanate and polyol. However, other amounts of the oil may also be used.

In certain embodiments, the polyurethane layer is formed in the presence of a silicone surfactant, i.e., the reaction mixture can include the silicone surfactant. Typically, the silicone surfactant comprises a polyorganosiloxane. A non-limiting example of a suitable polyorganosiloxane is an alkyl pendant organosilicone molecule comprising a polysiloxane backbone and polyether side chains. The alkyl pendant organosilicone molecule can be comb or dendrimer structured.

Without being bound or limited by any particular theory, it is thought that the silicone surfactant improves wetting of the polyol and isocyanate on the core particle. Accordingly, the silicone surfactant may also be a wetting agent. It is also thought that the silicone surfactant further improves adhesion of the polyurethane layer to the core particle. In addition, it is also thought that the silicone surfactant further reduces clumping and agglomeration of the encapsulated particle during and after the encapsulation process. The silicone surfactant is optional.

Generally, the yield of encapsulated particles is a measurement of the amount of encapsulated particles that pass through a sieve having 4 mm mesh and have a consistent polyurethane layer disposed thereabout. If utilized, the silicone surfactant generally decreases agglomeration of the core particles thereby increasing the yield of encapsulated particles. The encapsulation process typically maximizes the amount of encapsulated particles which are individually formed and free flowing and minimizes the amount of encapsulated particles which are agglomerated, therefore resulting in higher overall yield of encapsulated particles.

In certain embodiments, the silicone surfactant is a liquid and has a viscosity of from about 100 to about 1500, about 200 to about 1,000, or about 650 to about 850, cP at 25° C. The viscosity of the silicone surfactant may vary outside of the ranges above, but is typically both whole and fractional values within those ranges.

Specific examples of suitable silicone surfactants include TEGOSTAB® BF 2370, commercially available from Goldschmidt AG of Essen, DE; DABCO® DC5043, commercially available from Air Products and Chemicals, Inc. of Allentown, Pa.; and NIAX® Silicone L-5340 and L-620, both commercially available from Momentive Performance Materials of Albany, N.Y. A particularly suitable silicone surfactant is NIAX® Silicone L-620, which is a polyalkyleneoxidemethylsiloxane copolymer.

If utilized, the silicone surfactant may be present in the polyurethane layer in an amount of from about 0.01 to about 10, about 0.05 to about 5, or about 0.1 to about 3, parts by weight, each based on 100 parts by weight of the polyurethane layer. The parts by weight silicone surfactant may vary outside of the ranges above, but is typically both whole and fractional values within those ranges.

The polyurethane layer may optionally include one or more additives, i.e., the reaction mixture may include one or more additives. Suitable additives include chain-extenders, cross-linkers, chain-terminators, processing additives, adhesion promoters, anti-oxidants, defoamers, flame retardants, catalysts, anti-foaming agents, water scavengers, molecular sieves, fumed silicas, surfactants, ultraviolet light stabilizers, fillers, thixotropic agents, silicones, colorants, pigments, inert diluents, and combinations thereof. For example, a pigment can be included in the polyurethane layer to impart a color to the encapsulated particle. If utilized, the additive(s) can be included in the polyurethane layer in various amounts.

In certain embodiments, the polyurethane layer is present in the encapsulated particle in an amount of from about 1 to about 30, about 1 to about 20, about 1 to about 15, about 1 to about 10 about 1 to about 5, or about 2 to about 5, % by weight, each based on the total weight of the core particle. The amount of polyurethane layer present in the encapsulated particle may vary outside of the ranges above, but is typically both whole and fractional values within those ranges.

The amount of the polyurethane layer present in the encapsulated particle is typically determined using the following test procedure. Initially, 20 grams of the encapsulated particle and 500 grams of water, e.g. deionized water, are poured into a standard household blender. The blender is activated and the contents of the blender are mixed until the core particle, e.g. urea, is completely dissolved. The contents of the blender are then filtered for solids using pre-weighed filter paper and a Büchner funnel. The filtrand (or retentate) is then dried at approximately 100° C. to substantially remove residual water present with the filtrand. Typically, the filtrand is dried at 100° C. (e.g. in an oven) for approximately 30 minutes. After drying, the filtrand is weighed.

The amount (% by weight based on the total weight of the core particle) of the polyurethane layer present in the encapsulated particle is calculated using the amount (in grams) of the filtrand (X) and the amount (in grams) of the core particle (Y) in the following formula:

Polyurethane Layer (% by weight)=100·(X/Y)

wherein X=the amount of the filtrand (in grams) after drying, and Y=20 (initial amount of the encapsulated particle)−X.

In certain embodiments, the encapsulated particle includes a wax. In these embodiments, the wax is typically disposed on the polyurethane layer, opposite the core particle. The wax may encapsulate a portion or an entirety of the polyurethane layer, if utilized. Suitable examples of waxes include organic waxes, thermoplastic polymers, mineral oils, or combinations thereof. More particularly, the wax may comprise paraffinic oil, paraffinic wax, vegetable wax, triglyceride, microcrystalline wax, petrolatum, olefin, polyethylene, petroleum wax, and combinations thereof. In certain embodiments, the wax comprises a petroleum wax. In further embodiments, the wax comprises a petroleum wax and at least one additional wax different from petroleum wax. Wax is optional.

The encapsulated particle, optionally including the wax, is typically either round or roughly spherical. A plurality of encapsulated particles typically has a size distribution reported as D[4,3], d(0.1), d(0.5), and/or d(0.9). In certain embodiments, the encapsulated particles have a size distribution D[4,3] of from about 0.5 to about 5, about 1 to about 4, or about 1 to about 3, mm, with an overall particle size range of from about 0.1 to about 10 mm. In other embodiments, the encapsulated particles have a size distribution d(0.1) of from about 0.2 to about 2, about 0.4 to about 1.7, or about 0.5 to about 1.5, mm, with an overall particle size range of from about 0.1 to about 10 mm. In yet other embodiments, the encapsulated particles have a size distribution d(0.5) of from about 0.5 to about 5 mm, about 1 to about 4 mm, or about 1 to about 3, mm, with an overall particle size range of from about 0.1 to about 10 mm. In still yet other embodiments, the encapsulated particles have a size distribution d(0.9) of from about 0.7 to about 7, about 0.8 to about 5, or about 1 to about 4, mm, with an overall particle size range of from about 0.1 to about 10 mm. The D[4,3], d(0.1), d(0.5), and d(0.9) size distributions of the encapsulated particles may vary outside of the ranges above, but are typically both whole and fractional values within those ranges.

The polyurethane layer of the encapsulated particle impacts the controlled release of the core particle. A "greenhouse" test is used to determine whether the encapsulated particle adequately releases that which comprises the core particle in a controlled manner for a period of time. More specifically, plots of soil approximately 2 ft. by 2 ft. are seeded with crabgrass seed such that at least 80% of the surface of each plot is covered with crabgrass seed. The encapsulated particles are then applied to the plots at a rate of 1.5 lb ai/A (pounds active ingredient per acre). Air temperature around the plots is maintained at about 75 to about 80° F. The plots are watered once per day with ⅛ in. of water. The plots are monitored for crabgrass emergence daily for one week. Those plots treated with the encapsulated particle typically have less than about 10% and alternatively less than about 5% of the surface of each plot covered by crabgrass.

The encapsulated particle typically has a transferrable-pesticide transfer rate of 2.0 or less on a scale of 0.0 to 5.0. Transferrable-pesticide transfer rate is determined using a "sock test". More specifically, the encapsulated particles are applied to plots of grass approximately 3 ft. by 5 ft. at a rate of 1.5 lb ai/A. The plots are allowed to stand for approximately 1 hour prior to an individual placing white socks over their footware and shuffling, i.e., dragging their feet, through each plot, each time with a fresh pair of white socks. The socks are then rated on a prepared color scale of 0.0 to 5.0 based on intensity of color exhibited on the socks. For example, pendimethalin is yellow in color.

Also disclosed is a method of encapsulating the core particle with the polyurethane layer, and more specifically a method of forming the encapsulated particle. The method includes the steps of encapsulating the core particle with the transferrable-pesticide to form an intermediate-particle, combining the isocyanate and polyol to form the reaction mixture having a maximum temperature of no greater than about 30° C., and encapsulating the intermediate-particle with the reaction mixture to form the polyurethane layer of the encapsulated particle.

In certain embodiments, encapsulating the core particle with the transferrable-pesticide is further defined as encapsulating the core particle with the transferrable-pesticide at a temperature of less than or equal to about 30° C. and alternatively less than or equal to about 25° C. The transferrable-pesticide may be contained in a carrier or solvent, and encapsulating the core particle with the transferrable-pesticide may be further defined as encapsulating the core particle with the transferrable-pesticide in a carrier or a solvent.

The isocyanate and polyol are generally combined and/or mixed to form the reaction mixture and the isocyanate and polyol chemically react to form the polyurethane. Mixing and reacting the isocyanate and polyol can be conducted prior to encapsulating the transferrable-pesticide and the core particle with the polyurethane layer. Alternatively, mixing and reacting the isocyanate and polyol can be conducted simultaneous with encapsulating the transferrable-pesticide and the core particle with the polyurethane layer.

The isocyanate and polyol may be combined using one or more techniques including pouring, pan coating, fluidized-bed coating, co-extrusion, mixing, spraying and spinning disk encapsulation. In various embodiments, the isocyanate and polyol are mixed by spraying into or above a reaction vessel such as a barrel, a drum, mixer, or the like. The isocyanate and polyol can be mixed and sprayed into or above the reaction vessel with a single spray gun or multiple spray guns. In specific embodiments, the isocyanate and polyol are impingement mixed via a spray nozzle. The isocyanate and polyol can also be sequentially sprayed into or above the reaction vessel with a single spray gun and mixed in the reaction vessel. Alternatively, the isocyanate and polyol can be simultaneously or sequentially sprayed into or above the reaction vessel with different spay guns. Spraying the isocyanate and polyol tends to reduce agglomeration of the core particle and results in improved yield of the encapsulated particle.

In specific embodiments, mixing and reacting the isocyanate and polyol is further defined as mixing and reacting the isocyanate and polyol free of catalysts. In another embodiment, the isocyanate and polyol are mixed and reacted at a temperature that does not exceed 25° C.

The method optionally includes the steps of spraying the isocyanate onto the core particle and spraying the polyol onto the core particle. Spraying the isocyanate onto the core particle can be conducted prior to spraying the polyol onto the core particle. Alternatively, spraying the isocyanate onto the core particle can be conducted subsequent to spraying the polyol onto the core particle. Spraying the isocyanate onto the core particle can also be conducted prior to spraying the polyol onto the core particle and repeated after spraying the polyol onto the core particle. It is also contemplated that the isocyanate and polyol can be sprayed simultaneously and/or sequentially numerous times in various sequences onto the core particle and onto each other to form the polyurethane layer (or sub-layers).

As just one non-limiting example, the isocyanate and polyol can be sprayed onto the core particle in the following sequence: (1) a portion of the isocyanate is sprayed onto the core particle; (2) a portion of the of the polyol is sprayed onto the core particle; (3) a remaining portion of the isocyanate is sprayed onto the core particle; and (4) a remaining portion of the polyol is sprayed onto the core particle. As another example, the isocyanate and polyol can be sprayed onto the core particle in the following sequence: (1) a portion of the isocyanate is sprayed onto the core particle; (2) a portion of the of the polyol is sprayed onto the core particle and a remaining portion of the isocyanate is sprayed onto the core particle simultaneously; and (3) a remaining portion of the polyol is sprayed onto the core particle.

In another embodiment, the silicone surfactant is provided with the isocyanate, with the polyol, and/or provided independently. In another embodiment, the silicone surfactant can be used to pre-treat the surface of the core particle prior to encapsulation. In still another embodiment, the silicone surfactant is provided with the polyol, e.g. mixed with the polyol prior to mixing the isocyanate and polyol. In other words, the silicone surfactant can be provided in multiple ways.

In various embodiments, the isocyanate and the polyol are reacted at an isocyanate index of greater than about 70, from about 70 to about 130, about 80 to about 120, or about 90 to about 110. The isocyanate index may vary outside of the ranges above, but is typically both whole and fractional values within 70 to 130. Isocyanate index is a ratio of an actual molar amount of isocyanate(s) reacted with the polyol(s) to a stoichiometric molar amount of isocyanate(s) needed to react with an equivalent molar amount of the polyol(s).

Encapsulating the transferrable-pesticide and the core particle with the polyurethane layer can occur once or can be repeated. If repeated, the step does not have to be the same each individual time. The core particle may be encapsulated one time with a single polyurethane layer or multiple times with multiple polyurethane sub-layers. It is contemplated that the core particle can be encapsulated with at least one polyurethane sub-layer and one or more additional sub-layers including a material other than polyurethane. In certain embodiments, the polyurethane layer is disposed at least about 75, at least about 80, at least about 85, at least about 90, at least about 95, at least about 99, or at least 100, % of the core particle, or any % in between. Said differently, the core particle may be partially or completely encapsulated by the polyurethane layer.

The method optionally includes the step of agitating the encapsulated particle to reduce agglomeration, after the polyol and isocyanate are mixed to encapsulate the core particle. The encapsulated particle may be agitated in the reaction vessel or in any container. In various embodiments, the encapsulated particle is agitated in a mechanical mixer, such as a ribbon blender, a plough blender, a processing mixer, an impingement mixer, a rotating drum mixer, and combinations thereof. The step of agitating the encapsulated particle may include stirring the encapsulated particle, mixing the encapsulated particle, shaking the encapsulated particle, and combinations thereof. In certain embodiments, the encapsulated particle is agitated for a period of time of from about 0.5 to about 60, about 2 to about 30, about 4 to about 20, minutes, or any period of time in between.

In certain embodiments, the method further includes the steps of providing a wax and encapsulating the polyurethane layer with the wax. Typically, the wax is provided and melted. The molten wax is then added to the core particle having the polyurethane layer disposed thereon to further form the encapsulated particle. Typically, after the molten wax is added to the core particle having the polyurethane layer disposed thereon, the core particle is agitated until the molten wax cools and solidifies to form the encapsulated particle.

In particular embodiments, the core particle includes nitrogen fertilizer such as urea. In this embodiment, the core particle is loaded into a rotating drum. The catalytic polyol and polyether polyol are pre-blended to form the polyol, and the polyol, additives (if present), and silicone surfactant (if present), are pre-blended to further form the polyol. If present, the silicone surfactant, e.g. NIAX® L-620, is added to the polyol in an amount of 1 part by weight based on 100 parts by weight of the polyol. The isocyanate and polyol are sprayed sequentially onto the core particle at an isocyanate index of about 70 to about 130 and the formation of the polyurethane layer occurs with no additional heating, i.e., at ambient temperatures. In this embodiment, one half of the isocyanate is sprayed onto the core particle and the contents of the drum are agitated for 1 to 5 minute(s). Subsequently, all of the polyol is sprayed onto the core particle and the contents of the drum are agitated for another 1 to 5 minute(s). A remaining portion of the isocyanate is sprayed onto the core particle and the contents of the drum are agitated for another 5 to 10 minutes. Optionally, the contents of the drum are removed, added to a vessel, and preheated to 180° F. where molten wax is added to the vessel. The contents of the vessel are agitated until cooled to ambient temperature and the molten wax solidifies thereby forming the encapsulated particle.

The following examples, illustrating the encapsulated particles and method, are intended to illustrate and not to limit the invention.

EXAMPLES

Invention Encapsulated Particles 1 and 2 and Comparative Particles 1 and 2 are described hereinafter. Invention Encapsulated Particles 1 and 2 are encapsulated particles formed in accordance with the instant disclosure.

To form Invention Encapsulated Particles 1 and 2, a transferrable-pesticide is disposed about a core particle and a polyurethane layer is disposed about the transferrable-pesticide. The compositions used to form Invention Encapsulated Particles 1 and 2, in grams and weight percent, are set forth in Table 1 below. A polyol is provided in a first vessel. An isocyanate is provided in a second vessel. The core particle having the transferrable-pesticide disposed thereon is provided in a third vessel. Each of the polyol, isocyanate, and core particle are provided at ambient temperature, less than or equal to 25° C. The core particle is added to a reaction vessel that is not heated. Subsequently, the polyol is added to the reaction vessel and agitated (using a wooden tongue depressor) for 2 minutes with the core particle. Next, all of the isocyanate is added to the reaction vessel, and agitated with the polyol and core particle previously added, for 5 minutes. During agitation, the polyol and isocyanate react to form polyurethane. The reaction mixture does not exceed 25° C. As such, the core particle having the transferrable-pesticide disposed thereon is encapsulated with a polyurethane layer comprising the polyurethane. Said another way, the polyurethane layer is the reaction product of the isocyanate and polyol.

Comparative Particle 1 is a core particle having a transferrable-pesticide disposed thereon but is not encapsulated with a polyurethane layer. Comparative Particle 2 is a liquid suspension of transferrable-pesticide which is microencapsulated.

Invention Encapsulated Particles 1 and 2 and Comparative Particles 1 and 2 are evaluated to determine performance properties regarding transfer of the transferrable-pesticide. Additionally, Invention Encapsulated Particles 1 and 2 are evaluated to determine performance properties including agglomeration (clumping) and controlled release. The results of the evaluations are set forth in Table 2 below.

TABLE 1

|  | Invention Particle 1 | Invention Particle 2 |
| --- | --- | --- |
| Polyol A (g) | 1 | 0 |
| Polyol B (g) | 0 | 1 |
| Transferrable-pesticide (wt. % of Core Particle) | 1.2 | 1.2 |
| Isocyanate (g) | 1 | 1 |
| Core Particle (g) | 100 | 100 |
| Total (g) | 102 | 102 |
| Number of Polyurethane Layers | 1 | 1 |
| Polyurethane Layer (wt. %) | 2 | 2 |

TABLE 2

|  | Invention Particle 1 | Invention Particle 2 | Control | Comparative Particle 1 | Comparative Particle 2 |
| --- | --- | --- | --- | --- | --- |
| Agglomeration | Good | Good | N/A | N/A | N/A |
| Transfer of Transferrable pesticide | 2.0 | 1.2 | 0.0 | 2.3 | 2.7 |
| Efficacy | Yes | Yes | N/A | N/A | N/A |

Control has nothing applied to test plot.

Polyol A is an aromatic amine-initiated polyol having a nominal functionality of 4, nominal molecular weight of 500, OH number of 438-465 mg KOH/gm, and viscosity of 5,500 cps at 25° C., which is commercially available from BASF Corporation.

Polyol B is a polyether polyol having a nominal functionality of 3, nominal molecular weight of 400, OH number of 388-408 mg KOH/gm, and viscosity of 360 cps at 25° C., which is commercially available from BASF Corporation.

Transferrable-pesticide is pendimethalin, as described below with respect to the Core Particle.

Isocyanate is a polymeric methylene diphenyl diisocyanate (pMDI) having a nominal functionality of 2.7, NCO % of 31.5, and viscosity of 200 cps at 25° C., which is commercially available from BASF Corporation.

Core Particle is Scotts® Turf Builder® with Halts® Crabgrass Preventer, a core particle comprising urea, ammonium sulphate, sulphur, and potassium sulphate having pendimethalin disposed thereon, which is commercially available from Scotts of Marysville, Ohio. The pendimethalin is present in an amount of about 1.2 weight percent based on the total weight core particle.

Comparative Particle 1 is the same as Core Particle.

Comparative Particle 2 is AquaCap™, a liquid suspension of microencapsulated pendimethalin, which is commercially available from BASF Corporation.

Agglomeration is determined based on an objective observation of the Encapsulated Particles as they are passed through a sieve having 4 mm mesh. When the Encapsulated Particles agglomerate or clump together such that they do not pass through the sieve, an observation of "clumps" is recorded. Alternatively, when the Encapsulated Particles pass through the sieve freely, an observation of "good" is recorded. Agglomeration is typically indicative of reduced yield of the encapsulated particle and higher dissolution rates of the core particle.

Referring to Table 2, Invention Encapsulated Particles 1 and 2 have excellent performance properties. More specifically, Invention Encapsulated Particles 1 and 2 generally do not agglomerate, minimize transfer of the Transferrable-pesticide, and exhibit controlled release of the core particle.

Efficacy is determined using a "greenhouse" test. Plots of soil approximately 2 ft. by 2 ft. are seeded with crabgrass seed such that at least 80% of the surface of each plot is covered with crabgrass seed. The encapsulated particles are then applied to the plots at a rate of 1.5 lb ai/A. Air temperature around the plots is maintained at about 75 to about 80° F. The plots are watered once per day with ⅛ in. of water. The plots are monitored for crabgrass emergence daily for one week. The plots treated with Invention Particles 1 and 2 had less than 5% of the surface of the plot covered with crabgrass after one week whereas untreated plots had more than 80% of the surface of the plot covered with crabgrass after one week.

Transferrable-pesticide Transfer is determined using a "sock test". Invention Particles 1 and 2 and Comparative Particles 1 and 2 are applied to different plots of grass approximately 3 ft. by 5 ft. in area at a rate of 1.5 lb ai/A. The plots are allowed to stand for approximately 1 hour after application of the Invention and Comparative particles. Subsequently, an individual, with white socks placed over their footwear, shuffles, i.e., drags their feet, through each plot, each time with a fresh pair of white socks. The socks are then rated on a prepared pendimethalin color scale of 0.0 to 5.0 based on intensity of color exhibited on the socks. As shown in Table 2 above, Invention Particles 1 and 2 exhibited reduced transfer of transferrable-pesticide as compared to Comparative Particles 1 and 2.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the instant disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the instant disclosure, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The instant disclosure has been described herein in an illustrative manner, and it is to be understood that the terminology which has been used is intended to be in the nature of words of description rather than of limitation. Many modifications and variations of instant disclosure are possible in light of the above teachings. The instant disclosure may be practiced otherwise than as specifically described within the scope of the appended claims. The subject matter of all combinations of independent and dependent claims, both single and multiple dependent, is herein expressly contemplated.

What is claimed is:

1. An encapsulated particle comprising:
    a core particle comprising a fertilizer;
    a transferrable-pesticide having a vapor pressure of at least about 3 mPa at 25° C. and disposed about and in contact with said core particle; and
    a polyurethane layer having a glass transition temperature (Tg) of at least about 80° C., said polyurethane layer disposed about said transferrable-pesticide;
    wherein said polyurethane layer comprises the reaction product of an isocyanate and a polyol, and wherein the maximum temperature of a reaction mixture of said isocyanate and said polyol is no greater than about 25° C. during formation of said polyurethane layer.

2. The encapsulated particle as set forth in claim 1, wherein said polyurethane layer:
    i) comprises the reaction product of an isocyanate and a polyol; and
    ii) is free of catalyst(s).

3. The encapsulated particle as set forth in claim 2, wherein said polyol comprises the reaction product of i) an alkylene oxide having from 2 to 4 carbon atoms and ii) glycerol.

4. The encapsulated particle as set forth in claim 2, wherein said polyol has:
    i) a hydroxyl number of from about 200 to about 600 mg KOH/g; and/or
    ii) a viscosity of from about 100 to about 1,000 cPs at 25° C.; and/or
    iii) a number average molecular weight (Mn) of from about 200 to about 600 g/mol.

5. The encapsulated particle as set forth in claim 1, wherein said transferrable-pesticide comprises a dinitroaniline.

6. The encapsulated particle as set forth in claim 1, wherein said core particle comprises urea.

7. An encapsulated particle comprising:
    a core particle comprising a fertilizer;
    a transferrable-pesticide having a vapor pressure of at least about 3 mPa at 25° C. and disposed about said core particle; and
    a polyurethane layer having a glass transition temperature (Tg) of at least about 80 ° C. and formed from a reaction mixture having a maximum temperature of no greater than about 25° C., said polyurethane layer disposed about said transferrable-pesticide;

wherein said polyurethane layer inhibits said transferrable-pesticide from transferring to a surface different from said core particle when said encapsulated particle physically contacts the surface.

8. The encapsulated particle as set forth in claim 7, wherein said polyurethane layer:
   i) comprises the reaction product of an isocyanate and a polyol; and/or
   ii) is free of catalyst(s).

9. The encapsulated particle as set forth in claim 8, wherein said polyol comprises the reaction product of i) an alkylene oxide having from 2 to 4 carbon atoms and ii) glycerol.

10. The encapsulated particle as set forth in claim 7, wherein said transferrable-pesticide comprises a dinitroaniline.

11. The encapsulated particle as set forth in claim 7, wherein said core particle comprises urea.

12. A method of forming an encapsulated particle comprising a core particle comprising a fertilizer, a transferrable-pesticide having a vapor pressure of at least about 3 mPa at 25° C. and disposed about and in contact with the core particle, and a polyurethane layer having a glass transition temperature (Tg) of at least about 80 ° C. disposed about the transferrable-pesticide, wherein the core particle comprises a fertilizer, and the polyurethane layer comprises the reaction product of an isocyanate and a polyol, said method comprising the steps of:
   encapsulating the core particle with the transferrable-pesticide to form an intermediate-particle;
   combining the isocyanate and the polyol to form a reaction mixture having a maximum reaction temperature of no greater than about 25° C.; and
   encapsulating the intermediate-particle with the reaction mixture to form the polyurethane layer of the encapsulated particle.

13. The method as set forth in claim 12, wherein the transferrable-pesticide comprises a dinitroaniline or is pendimethalin.

14. The method as set forth in claim 12, wherein the reaction mixture of the polyurethane layer:
   i) is free of catalyst(s); and/or
   ii) further comprises a silicone surfactant.

* * * * *